US007635481B2

(12) United States Patent
Hu et al.

(10) Patent No.: US 7,635,481 B2
(45) Date of Patent: Dec. 22, 2009

(54) CANINE VACCINE FOR PROTECTION AGAINST EHRLICHIOSIS

(75) Inventors: Liangbiao (George) Hu, Wildwood, MO (US); Thomas J. Hess, Fort Dodge, IA (US); Yu-Wei Chiang, Fort Dodge, IA (US); Hsien-Jue (Steve) Chu, Fort Dodge, IA (US)

(73) Assignee: Wyeth, Madison, NJ (US)

( * ) Notice: Subject to any disclaimer, the term of this patent is extended or adjusted under 35 U.S.C. 154(b) by 0 days.

(21) Appl. No.: 11/407,558

(22) Filed: Apr. 20, 2006

(65) Prior Publication Data

US 2006/0188524 A1 Aug. 24, 2006

Related U.S. Application Data

(63) Continuation of application No. 11/076,278, filed on Mar. 9, 2005, now abandoned.

(60) Provisional application No. 60/552,350, filed on Mar. 11, 2004.

(51) Int. Cl.
*A61K 39/02* (2006.01)
*A61K 39/38* (2006.01)
*A61K 45/00* (2006.01)

(52) U.S. Cl. .............. 424/190.1; 424/184.1; 424/278.1

(58) Field of Classification Search .............. 424/190.1, 424/184.1, 278.1
See application file for complete search history.

(56) References Cited

U.S. PATENT DOCUMENTS

| 5,192,679 A | 3/1993 | Dawson et al. |
| 6,043,085 A | 3/2000 | Yu et al. |
| 6,432,649 B1 | 8/2002 | Stich et al. |
| 6,458,942 B1 * | 10/2002 | Walker et al. .............. 536/23.5 |
| 2003/0129161 A1 * | 7/2003 | Chu .......................... 424/85.2 |

FOREIGN PATENT DOCUMENTS

WO WO 98/42743 A1 * 10/1998

OTHER PUBLICATIONS

Boslego, J. et al (Gonorrhea Vaccines, Chapter 17, 211-223).*
Ellis, R (New Technologies for Making Vaccines, text book, 1998, 568-575).*
Maender et al (Treatment and prevention of rickettsial and ehrlichial infections, Dermatological Therapy, 2004; 17: 499-504).*
Nash, H., Ehrlichiosis in Dogs, http://www.peteducation.com, p. 1-3).*
Rikihisam, Y., Human Ehrichiosis, Ohio State University, http://riki-1b1.vet.ohio-state.edu/ehrlichia/background/ehrlichiosis.php, pp. 1-2.*
Keysary et al., "The first isolation, in vitro propagation, and genetic characterization of *Ehrlichia canis* in Israel," Veterinary Parasitology, vol. 62, 1996, pp. 331-340.
McBride et al., "Glycosylation of Homologous Immunodominant Proteins of *Ehrlichia chaffeensis* and *Ehrlichia canis*," Infection and Immunity, vol. 68, No. 1, Jan. 2000, pp. 13-18.
Bowie et al., "Potential Value of Major Antigenic Protein 2 for Serological Diagnosis of Heartwater and Related Ehrlichial Infections," Clinical and Diagnostic Laboratory Immunology, vol. 6, No. 2, Mar. 1999, pp. 209-215.
Unver et al., "Molecular and Antigenic Comparison of *Ehrlichia canis* Isolates from Dogs, Ticks, and a Human in Venezuela," Journal of Clinical Microbiology, vol. 39, No. 8, Aug. 2001, pp. 2788-2793.
Mathew et al., "Attempted transmission of *Ehrlichia canis* by *Rhipicephalus sanguineus* after passage in cell culture," American Journal of Veterinary Research, vol. 57, No. 11, Nov. 1996, pp. 1594-1598.
Dawson et al., "Serologic Diagnosis of Human Ehrlichiosis Using Two *Ehrlichia canis* Isolates," Journal of Infectious Diseases, vol. 163, 1991, pp. 564-567.
Keysary et al., "Cultivation of *Ehrlichia canis* in a continuous BALB/C mouse macrophage cell culture line," Journal of Veterinary Diagnostic Investigation, vol. 13, 2001, pp. 521-523.
Unver et al., "Analysis of 16S rRNA Gene Sequences of *Ehrlichia canis, Anaplasma platys,* and *Wolbachia* Species from Canine Blood in Japan," Annals of New York Academy of Sciences, vol. 990, 2003, pp. 692-698.
Dancey et al., "Effect of Liposomal Model Membrane Composition on Immunogenicity," The Journal of Immunology, vol. 120, No. 4, Apr. 1978, pp. 1109-1113.
Allison et al., "Liposomes as immunological adjuvants," Nature, vol. 252, Nov. 15, 1974, pp. 252-254.
McBride et al., "Kinetics of Antibody Response to *Ehrlichia canis* Immunoreactive Proteins," Infection and Immunity, vol. 71, No. 5, May 2003, pp. 2516-2524.
Mwangi et al., "Immunization of Cattle by Infection with *Cowdria ruminantium* Elicits T Lymphocytes That Recognize Autologous, Infected Endothelial Cells and Monocytes," Infection and Immunity, vol. 66, No. 5, May 1998, pp. 1855-1860.
Rikihisa, Y., "Protection Against Murine Potomac Horse Fever by an Inactivated *Ehrlichia risticii* Vaccine," Veterinary Microbiology, vol. 27, 1991, pp. 339-350.
Hemelt et al., "Serial propagation of *Ehrlichia canis* in primary canine peripheral blood monocyte cultures," The Cornell Veterinarian, vol. 70, No. 1, Jan. 1980, pp. 36-42.

(Continued)

*Primary Examiner*—Robert B Mondesi
*Assistant Examiner*—Lakia J Tongue
(74) *Attorney, Agent, or Firm*—Adley F. Mandel; Anne M. Rosenblum

(57) ABSTRACT

The present invention provides a safe and effective vaccine composition which comprises: an effective immunizing amount of an inactivated *Ehrlichia canis* bacterin; a pharmacologically acceptable carrier; and an immunogenically stimulating amount of an adjuvant system consisting essentially of an antibody response inducing agent and a cell-mediated immunity response inducing agent.

The present invention also provides a method for the prevention or amelioration of canine ehrlichiosis in dogs.

12 Claims, No Drawings

OTHER PUBLICATIONS

Kakoma et al., "Autologous lymphocyte-mediated cytotoxicity against monocytes in canine ehrlichiosis," American Journal of Veterinary Research, vol. 38, No. 10, Oct. 1977, pp. 1557-1559.

Nyindo et al., "Cell-mediated and humoral immune responses of German Shepherd Dogs and Beagles to experimental infection with *Ehrlichia canis*.," American Journal of Veterinary Research, vol. 41, No. 2, 1980, pp. 250-254.

Esteves et al., "Analysis of *Ehrlichia ruminantium*-specific T1/T2 responses during vaccination with a protective killed vaccine and challenge of goats," Parasite Immunology, vol. 26, No. 2, Feb. 2004, pp. 95-103.

Boslego et al., Chapter 17, Gonorrhea Vaccines, 1991, pp. 211-223, in Vaccines and Immunotherapy, Pergamon press, Edited by Stanley J. Cryz, Jr.

Ellis, R., Chapter 29, New Technologies for Making Vaccines, 1998, pp. 568-575, in Vaccines, WB Sunders Company.

Maender et al., "Treatment and prevention of rickettsial and ehrlichial infections," Dermatological Therapy, vol. 17, 2004, pp. 499-504.

Nash, H., "Ehrlichiosis [in Dogs]," Veterinary Services Department, Drs. Foster & Smith, Inc., http://www.peteducation.com, pp. 1-3, Oct. 13, 2005.

Rikihisa, Y. (Primary Investigator), "Human Ehrlichiosis," Ehrlichial Research Laboratory, Department of Veterinary Biosciences, Ohio State University, http://riki-lb1.vet.ohio-state.edu/ehrlichia/background/ehrlichiaspp.php, pp. 1-2, Oct. 13, 2005.

* cited by examiner

CANINE VACCINE FOR PROTECTION AGAINST EHRLICHIOSIS

This is a continuation application of U.S. application Ser. No. 11/076,278, filed on Mar. 9, 2005, now abandoned which claims the priority benefit under 35 U.S.C. §119(e) of U.S. Provisional Application No. 60/552,350, filed on Mar. 11, 2004, abandoned, the entire disclosure of which is hereby incorporated by reference.

BACKGROUND OF THE INVENTION

Canine ehrlichiosis is a lethal disease caused by *Ehrlichia canis* (*E. canis*), a blood-borne intracellular pathogen, and infects all breeds of dogs at any growth phase. Canine ehrlichiosis is transmitted primarily by the brown dog tick, *Rhipicephalus sanguineous*, which is believed to be the primary reservoir for the disease. Canine ehrlichiosis is a potentially lethal disease that is endemic in the United States and occurs worldwide. Symptoms commonly progress from an acute to chronic disease state depending on the strain of the organism and immune status of the host. In acute cases, symptoms include mucopurulent ocular and nasal discharge, dehydration, reticuloendothelial hyperplasia, fever, generalized lymphadenopathy, splenomegaly and thrombocytopenia. In chronic cases, variable signs of anorexia, depression, loss of stamina, stiffness and reluctance to walk, edema of the limbs or scrotum, and coughing or dyspnea may occur.

There is currently no vaccine available for the effective treatment or prevention of canine ehrlichiosis. The common treatment for all forms of ehrlichiosis is administration of an antibiotic, such as tetracycline, for a minimum of 2 weeks for acute cases, or 1-2 months in chronic cases. In chronic cases, the hemotologic abnormalities may persist for 3-6 months, or for a lifetime. Supportive therapy may be necessary to combat wasting and specific organ dysfunction. Clearly, effective prevention of the disease would be preferred over a post-infection antibiotic regime.

Therefore, it is an object of this invention to provide a safe and effective vaccine composition useful for the induction of protective immunity against canine ehrlichiosis in dogs.

It is another object of this invention to provide a method for the prevention or amelioration of canine ehrlichiosis in dogs.

It is a further object of this invention to provide a method for the induction of clinical canine ehrlichiosis in a test animal. Said method is useful for the evaluation and study of host defenses and pathogenic mechanisms, and for the improved development of vaccines against ehrlichiosis.

It is a feature of this invention that the vaccine composition can protect dogs against multiple strains of *E. canis* originating in a variety of geographic regions.

It is another feature of this invention that effective protective immunity against canine ehrlichiosis may be imparted to dogs of any age.

Further objects and features of the invention will become apparent from the detailed description set forth hereinbelow.

SUMMARY OF THE INVENTION

The present invention provides a safe and effective vaccine composition which comprises: an effective immunizing amount of an inactivated *Ehrlichia canis* bacterin, a pharmacologically acceptable carrier, and an immunogenically stimulating amount of an adjuvant system comprising or consisting essentially of an antibody response inducing agent and a cell-mediated immunity (CMI) response inducing agent.

The present invention also provides a method for the prevention or amelioration of canine ehrlichiosis in dogs.

The present invention further provides a method for the induction of clinical *E. canis* infection in a test animal, which is useful for the study and evaluation of host defenses and pathogenic mechanisms, and for the advanced development of the treatment and prevention of canine ehrlichiosis.

DETAILED DESCRIPTION OF THE INVENTION

The causative agent of canine ehrlichiosis is *Ehrlichia canis* (*E. canis*), a Gram-negative bacteria of the order *Rickettsiales*, that occurs either singly or in compact inclusions in circulating mammalian leukocytes and is transmitted by ticks. Canine ehrlichiosis is endemic in many parts of the United States and is known to occur worldwide. Acute, naturally occurring canine ehrlichiosis mimics Rocky Mountain spotted fever. Most acute cases occur in the warmer months, which is coincident with the greatest activity of the tick vector. Canine ehrlichiosis can be a lethal disease. Very often it is a chronic disease that may affect a dog of any age causing variable symptoms such as anorexia, depression, loss of stamina, stiffness and a reluctance to walk, edema of the limbs or scrotum, coughing or dyspnea. Heretofore, there are no known effective vaccination or immunization treatments available against canine ehrlichiosis.

Surprisingly, it has now been found that a vaccine composition, which comprises an effective immunizing amount of an inactivated *E. canis* bacterin, a pharmacologically acceptable carrier, and an immunogenically stimulating amount of an adjuvant system consisting essentially of an antibody response inducing agent and a cell-mediated immunity (CMI) response inducing agent, may be administered to dogs at any growth stage to prevent or ameliorate canine ehrlichiosis, preferably at 16 weeks of age or older.

*E. canis* bacterin suitable for use in the vaccine composition of the invention may be of one or more strains. *E. canis* bacterin suitable for use in the vaccine composition of the present invention may be one or more strains, such as those designated as Ebony, Broadfoot, Fla., Israel 611, Kogashima 1, Louisiana, Oklahoma, Venezuela, the North Carolina State University (NCSU) strain Jake, the NCSU isolates Demon, D J and Fuzzy, *E. canis* infected cell lines with any of the designated strains, *E. canis* infected DH82 cell line with any of the designated strains or the *E. canis* infected DH82 cell line deposited with the American Type Culture Collection (ATCC, 10801 University Boulevard, Manassas, Va. 20110-2209 U.S.A.), and given the accession number CRL 10390, as disclosed in U.S. Pat. No. 5,192,679, or the like. An *E. canis* bacterin suitable for use in the vaccine composition of the present invention may preferably be two strains of *E. canis*, such as Ebony and Broadfoot.

The Ebony strain, for example, is 99.9 percent homologous with the Oklahoma strain based on the 16S recombinant DNA (rDNA) sequence (i.e., one nucleotide difference) [Mathew J S et al., Attempted transmission of *Ehrlichia canis* by *Rhipicephalus sanguineus* after passage in cell culture, Am J Vet Res 1996 November; 57(11):1594-8], and has been shown to be transmissible to dogs by nymphal and adult brown dog tick (*Rhipicephalus sanguineus*) (Mathew 1996).

The Florida strain has been disclosed to contain a conserved major immunoreactive 28-kDa protein gene (U.S. Pat. No. 6,458,942) and a p 30 gene belonging to the omp-1 multiple gene family (U.S. Pat. No. 6,432,649). Moreover, U.S. Pat. No. 6,043,085 discloses that the Florida strain has a 120-kDa immunodominant antigenic protein, containing 14 repeats with 36 amino acids each, which are predicted to be surface-exposed. The repeat units are hydrophilic that form the core of the surface exposed regions of the protein, and are rich in serine and glutamic acid. Serine and glutamic acid each comprise 19% of the amino acids of a repeat unit. The Florida strain is believed to be less virulent than the *E. canis* strain NCSU Jake [Breitschwerdt et al. Doxycycline hyclate treatment of experimental canine Ehrlichiosis followed by challenge inoculation with two *Ehrlichia canis* strains, Antimicrobial Agents and Chemotherapy, 1998 February; 42(2): 362-68], while serological comparison with the Oklahoma strain revealed 100% specificity and 87.5% sensitivity [Dawson J E et al. Serological comparison of human ehrlichiosis using two Ehrlichia canis isolates. J Infect Dis. 1991 March; 163(3):564-7].

In addition to being grown in a continuous canine cell line (e.g., DH82) (Keysary A et al. The first isolation, in vitro propagation, and genetic characterization of *Ehrlichia canis* in Israel, Vet. Parasitol. 1996 April; 62(3-4):331-40.), the Israel 611 strain has been grown in a continuous mouse macrophage cell line (e.g., J774.A1) (Keysary A et al. Cultivation of *Ehrlichia canis* in a continuous BALB/C mouse macrophage cell culture line, J Vet Diag. Invest. 2001 November; 13(6):521-3). Israel 611 has two forms of morulae: (1) tightly packed and (2) loosely packed, and its 16S rRNA gene sequence is three nucleotides different than the Oklahoma strain and four nucleotides different than the Florida strain, with a gap of one nucleotide in each (Keysary, 1996). The degree of homology difference from the Oklahoma strain is 0.54 percent while the difference from the Florida strain is 0.61 percent (Keysary, 1996).

Like the Florida strain, the Louisiana strain has a conserved major immunoreactive 28-kDa protein gene (U.S. Pat. No. 6,458,942), a p 30 gene belonging to the omp-1 multiple gene family (U.S. Pat. No. 6,432,649), and, as disclosed in U.S. Pat. No. 6,043,085, a 120-kDa immunodominant antigenic protein, containing 14 repeats with 36 amino acids each, which are predicted to be surface-exposed. The repeat units are hydrophilic that form the core of the surface exposed regions of the protein, and are rich in serine and glutamic acid. Serine and glutamic acid each comprise 19% of the amino acids of a repeat unit.

Also similarly, the Oklahoma strain has a conserved major immunoreactive 28-kDa protein gene (U.S. Pat. No. 6,458,942), a p 30 gene belonging to the omp-1 multiple gene family (U.S. Pat. No. 6,432,649), and, as disclosed in U.S. Pat. No. 6,043,085, a 120-kDa immunodominant antigenic protein, containing 14 repeats with 36 amino acids each, which are predicted to be surface-exposed. The repeat units are hydrophilic that form the core of the surface exposed regions of the protein, and are rich in serine and glutamic acid. Serine and glutamic acid each comprise 19% of the amino acids of a repeat unit. Additionally, McBride J W et al. found Oklahoma to possess a glycoprotein gene (2,064 bp) that encodes proteins of 548 to 688 amino acids with predicted molecular masses of only 61 and 73 kDa, but with electrophoretic mobilities of 140 kDa (P140), respectively. The 140-kDa protein gene has fourteen (14) nearly identical, tandemly arranged 108-bp repeat units. The 14-repeat region (78%) of the P140 gene (1,620 bp) was expressed in *Escherichia coli*. The recombinant protein exhibited molecular masses ranging from 1.6 to 2 times larger than those predicted by the amino acid sequences. Antibodies against the recombinant proteins react with *E. canis* P140. Carbohydrate was detected on the *E. canis* recombinant proteins. A carbohydrate compositional analysis identified glucose, galactose, and xylose on the recombinant proteins. The presence of only one site for N-linked (Asn-Xaa-Ser/Thr) glycosylation, a lack of effect of N-glycosidase F, the presence of 70 and 126 Ser/Thr glycosylation sites in the repeat regions of P120 and P140, respectively, and a high molar ratio of carbohydrate to protein suggest that the glycans may be O linked (McBride J W et al. Glycosylation of Homologous Immunodominant Proteins of *Ehrlichia chaffeensis* and *Ehrlichia canis*. Infection and Immunity, January 2000, 68(1):13-18). Oklahoma can be grown in the canine macrophage cell line DH82 in minimum essential medium containing 12.5% fetal bovine serum and 200 mM L-glutamine (Bowie, M. V. et al. Potential value of major antigenic protein 2 for serological diagnosis of heartwater and related *Ehrlichial* infections, Clin. Diagnostic Lab. Immun., 1999 March; 6(2):209-15). A serological comparison with FL strain revealed 100% specificity and 87.5% sensitivity (Dawson 1991, supra). Similarity of 99.9 percent, based on the 16S rDNA sequence, has been found with the strains Ebony (Mathew 1996), Kagoshima 1 (Unver A et al. Analysis of 16S rRNA gene sequences of *Ehrlichia canis, Anaplasma* platys, and *Wolbachia* species from canine blood in Japan, Ann NY Acad. Sci. 2003 June; 990:692-8), and Venezuela (Unver A et al. Molecular and antigenic comparison of *Ehrlichia canis* isolates from dogs, ticks, and a human in Venezuela. J Clin Microbiol. 2001 August; 39(8):2788-93).

For the NCSU isolates, Demon, D J and Fuzzy, and strain Jake, all possess a conserved major immunoreactive 28-kDa protein gene (U.S. Pat. No. 6,458,942). It has been disclosed that D J, Fuzzy and Jake also have p 30 gene belonging to the omp-1 multiple gene family (U.S. Pat. No. 6,432,649). Jake is believed to be more virulent than the Florida strain (Breitschwerdt 1998, supra).

Nearly the entire 16S rRNA sequence of Kagoshima 1 was found to be most similar to the sequences from Oklahoma and Venezuela *E. canis* strains (1 base pair difference out of 1,387) with a 99.9 percent sequence identity (Unver 2003, supra). In addition, and similarly, to its high sequence identity to the Kagoshima 1 strain, the Venezuela strain is 99.9 percent similar to the Oklahoma strain based on the 16S rDNA sequence (Unver 2001).

In preferred practice, the *E. canis* bacterin is grown in a canine monocyte macrophage cell line, sometimes referred to as continuous canine macrophage cells or canine macrophage cell line, supported by a medium containing RPMI1640 supplemented with fetal bovine serum, glucose and glutamine. Preferrably, the cells are cultured on a supporting medium which may be RPMI1640, OptiMEM, or AIM V, preferably RPMI1640, supplemented with up to 10% fetal bovine serum, 0.5% lactalbumin hydrolysate, 30 μg/mL Polymyxin B, 110 μg/mL sodium pyruvate, 2.5 mg/mL sodium bicarbonate, 4 mg/mL glucose, 6 mg/mL L-glutamine, 0.55 mg/mL magnesium sulfate, and cultured for up to 95 days, preferably for up to 35 days, most preferably about 5 to 10 days, to achieve a titer of $\geqq 1\times10^4$ $TCID_{50}$ (Tissue Culture Infectious Dose), and then the culture is harvested and processed for inactivation.

The thus-obtained *E. canis* bacterin can then be inactivated by conventional inactivation means. For example, chemical inactivation using chemical inactivating agents such as binary ethyleneimine, beta-propiolactone, formalin, merthiolate, gluteraldehyde, sodium dodecyl sulfate, or the like, or a mixture thereof, with formalin being the preferred inactivation agent. The bacterin may also be inactivated by heat or psoralen in the presence of ultraviolet light.

The effective immunizing amount of the inactivated *E. canis* bacterin can vary depending upon the chosen strain or strains and may be any amount sufficient to evoke a protective immune response. Amounts wherein the dosage unit comprises at least about $1 \times 10^4$ TCID$_{50}$ inactivated *E. canis* bacterin are suitable.

As used herein, the term "antibody response-inducing agent" designates any compound, or combination of compounds, capable of enhancing a humoral immunity response. Typical examples are ethylene maleic anhydrate (EMA) copolymer, latex emulsions of a copolymer of styrene with a mixture of acrylic acid and methacrylic acid, such as NEOCRYL® A-640 (Avecia Neo Resius, Frankfort, Ind.), aluminum hydroxide, or the like, or a mixture thereof. The antibody response-inducing agent of the present invention is preferably a mixture of EMA and NEOCRYL®. NEOCRYL® is a registered trade name of Avecia BV, Sluisweg 12 P.O. Box 123 NL-5140 AC Waalwijk Netherlands, for water borne acrylic polymers and copolymers. The numeral A640 denotes a grade thereof. NEOCRYL® A640 is an uncoalesced aqueous styrenated acrylic copolymer, having a pH of about 7.5, a viscosity of about 100 cps (Brookfield 25° C.), a weight per gallon of 8.6 pounds as supplied containing 40 percent solids by weight, a specific gravity of 1.30 mg/L, a glass transition temperature (Tg) of 44° C., a minimum film forming temperature (MFFT) of 40° C., and an acid number (nonvolatile) of 50. Specifically, NEOCRYL® A640 is an uncoalesced aqueous acrylic copolymer with styrene. More specifically, NEOCRYL® A640 is a latex emulsion of a copolymer of styrene with a mixture of acrylic and methacrylic acid.

Suitable grades of the EMA copolymer useful in this invention are the linear ethylene-maleic anhydride copolymers, such as EMA-31 (Monsanto Co., St. Louis, Mo.), which is an acid functional copolymer. These copolymers are water soluble, fine, white, free-flowing powders having the following typical properties: a softening point of about 170° C., a decomposition temperature of about 247° C., a pH (1% solution) of 2.3, and a specific viscosity (1% solution in dimethyl formamide) of 0.9-1.2 g/100 mL.

The term "cell-mediated immunity (CMI) response inducing agent," as used herein, designates any agent, or combination of agents, capable of enhancing a cellular immunity response. Typical examples are biologics, such as an attenuated strain of *Mycobacterium bovis*, Bacille Calmette-Guérin (BCG) (Calbiochem, La Jolla, Calif.) or the like, and Th1-related cytokines, such as interleukin-12 (IL-12), interleukin-18 (IL-18), gamma interferon or the like, preferably IL-12; or substances that are oil-in-water emulsions, such as a paraffin oil-in-water emulsion like EMULSIGEN® SA (MVP Laboratories, Ralston, Nebr.), SP oil (a composition of squalane, PLURONIC® L 121 and TWEEN® 80 (squalane is from VWR/Kodak, Rochester, N.Y., the PLURONIC® L121 available from BASF, Mt. Olive, N.J. and TWEEN® 80 is an emulsifying agent polysorbate available from Sigma Chemical Co., St. Louis, Mo.)), SAF-1 (Syntex Adjuvant Formulation-1, a composition of the threonyl analog of muramyl dipeptide, TWEEN® 80, PLURONIC® L121 and squalene, which is described by Byars, N. E. and Allison, A. C., Vaccine, 5(3):223-28) or the like, preferably, EMULSIGEN® SA and more preferably, an oil-in-water emulsion. EMULSIGEN® is a registered trademark of Modern Veterinary Products, 5404 Miller Ave. Omaha, Nebr. 68127, U.S.A., for veterinary antigen adjuvants of an emulsified oil-in-water nature. The letters SA denotes a grade thereof. EMULSIGEN® SA, a paraffin emulsified oil adjuvant base, is milky-white when mixed with Tryptic Soy Broth (TSB) (20% final concentration), with a viscosity of 25-50 cps (Brookfield LV viscometer, spindle #18, at 30 rpm), and comprises at least 80% of oil phase droplets less than or equal to eight (8) microns. PLURONIC® is a registered trademark of BASF Corporation for block copolymers of ethylene oxide and propylene oxide and the numeral L121 denotes a grade thereof.

Immunogenically stimulating amounts of the adjuvant system may vary according to the antibody response inducing agent, the CMI inducing agent, the *E. canis* bacterin component, the degree of potential infectious exposure, the method of administration of the vaccine composition, the growth stage and size of the dog, or the like. Moreover, immunogenically stimulating amounts of the adjuvant system are an amount that is sufficient to enhance an immune response to the immunizing agent—*E. canis* bacterin. In general, amounts of about 1% to 6% vol/vol, preferably about 4% vol/vol of the antibody response inducing agent and about 3% to 7% vol/vol, preferably about 5% vol/vol, of the CMI inducing agent are suitable.

Pharmacologically acceptable carriers suitable for use in the vaccine composition of the invention may be any conventional liquid carrier suitable for veterinary pharmaceutical compositions, and preferably is a balanced salt solution such as is suitable for use in tissue culture media.

In addition to the inactivated *E. canis* bacterin as active ingredient, it is contemplated the vaccine composition of the invention may also contain other active components such as an antipathogenic component directed against rabies virus, Lime disease (*Borrelia burgdorferi*), canine distemper virus, canine parvovirus, canine adenovirus, canine corona virus, *Giardia; leptospira interrogans* such as serovars *canicola, icterohaemorrhagiae, pomona, grippotyphosa* or *bratislava* or the like, or a combination thereof.

In one embodiment of the invention, the inactivated *E. canis* bacterin component of the invention may be incorporated into liposomes using known technology such as that described in *Nature*, 1974, 252, 252-254 or *Journal of Immunology*, 1978, 120, 1109-13. In another embodiment of the invention, the inactivated *E. canis* bacterin component of the invention may be conjugated to suitable biological compounds such as polysaccharides, peptides, proteins, or the like, or a combination thereof.

In a preferred embodiment of the invention, the inventive vaccine composition may be formulated in a dosage unit form to facilitate administration and ensure uniformity of dosage. Herein, a dosage unit as it pertains to the vaccine composition refers to physically discrete units suitable as unitary dosages for animals, each unit containing a predetermined quantity of *E. canis* bacterin calculated to produce the desired immunogenic effect in association with the required adjuvant system and carrier or vehicle.

The inventive vaccine composition may be administered parenterally, for example, intramuscularly, subcutaneously, intraperitoneally, intradermally or the like, preferably, subcutaneously or intradermally, and more preferably, subcutaneously; or said composition may be administered orally or intranasally.

Accordingly, the present invention also provides a method for the prevention or amelioration of canine ehrlichiosis in dogs which comprises administering to said dog a safe and effective vaccine composition as described hereinabove.

In preferred practice, the vaccine composition of the invention is administered parenterally, orally, or intranasally, preferably parenterally, more preferably subcutaneously, in effective amounts according to a schedule determined by the time of potential exposure to a carrier of the *E. canis* bacterin. In this way, the treated animal may have time to build immunity prior to the natural exposure. For example, a typical treatment schedule may include parenteral administration, preferably subcutaneous injection, at least 5 weeks prior to potential exposure. At least two administrations are preferred, for example, the first at about 5 weeks and a second at about 2 weeks prior to potential exposure of the treated animal.

In order to effectively study and evaluate the pathogenic mechanisms of the *E. canis* bacterin and the defense mechanisms of the host canine and thereby to advance the vaccine art and improve vaccine products, an effective challenge model must be created. Although different challenge models for canine ehrlichiosis are known, none has been effective in causing a high percentage of test animals to demonstrate persistent and severe clinical symptoms that are commonly associated with canine ehrlichiosis, such as mucopurulent ocular discharge, dehydration, or the like. Therefore, a better, more consistently effective challenge model is needed for the evaluation of vaccines and pharmaceuticals, and the study of *E. canis* bacterin and disease caused thereby.

Surprisingly, it has now been found that a particularly effective *E. canis* challenge may be obtained in a test animal by administering to said test animal a challenge stock of peripheral blood mononuclear cells (PBMC) containing a virulent culture of live *E. canis* bacteria. The virulent *E. canis* culture is prepared by repeatedly passaging the *E. canis* microorganism such as *E. canis* Ebony, *E. canis* Broadfoot or the like, preferably *E. canis* Ebony, in a host; separating the PBMC from the host blood sample; and mixing the separated PBMC with 20% fetal bovine serum and 10% dimethyl sulfoxide. Accordingly, the present invention also provides a method for the induction of clinical canine ehrlichiosis in a test animal which comprises administering to said animal an effective amount of an *E. canis* challenge stock, consisting essentially of a virulent *E. canis* microorganism in peripheral blood mononuclear cells. Viable cultures of each of *E. canis* Broadfoot (sometimes referred to as *E. canis* BF, or Broadfoot), and *E. canis* Ebony (sometimes referred to as Ebony) have been deposited (Feb. 11, 2004) with the ATCC, 10801 University Boulevard, Manassas, Va. 20110-2209 U.S.A. (under terms and requirements of the Budapest Treaty relating to the deposit of microorganisms for the purposes of a patent procedure), and have been respectively given the ATCC accession numbers PTA-5811 for the Broadfoot strain, and PTA-5812 for the Ebony strain.

In actual practice, the virulence of the *E. canis* microorganism is increased by repeated passages in a host animal. Whole blood samples from the host are placed on a gradient medium such as HISTOPAQUE® 1077, (a density gradient medium commerically available from Sigma-Aldrich Biotechnology LP, St. Louis, MO), centrifuged, and the PBMC layer is separated. The thus-obtained PBMC are admixed with 20% fetal bovine serum and 10% dimethyl sulfoxide and frozen in liquid nitrogen for storage to provide a consistent and continual supply of challenge stock. This challenge stock may be diluted with buffer saline solution prior to administration to a test animal. Administration may be by any conventional inoculation route such as subcutaneous, intramuscular, intradermal, or the like, and most preferably is by subcutaneous administration.

For a more clear understanding of the invention, the following examples are set forth below. These examples are merely illustrative and are not understood to limit the scope or underlying principles of the invention in any way. Indeed, various modifications of the invention, in addition to those shown and described herein, will become apparent to those skilled in the art from the examples set forth hereinbelow and the foregoing description. Such modifications are also intended to fall within the scope of the appended claims.

Unless otherwise noted, all parts are parts by weight.

EXAMPLE 1

Evaluation of a Virulent *E. canis* Challenge Model

A. Preparation of Challenge Stock

Live *E. canis* Ebony strain bacteria are repeatedly passaged in dogs. Whole blood samples from the infected dogs are centrifuged at 2500×g for 15 min. The buffy coat is collected and diluted with phosphate buffered solution (PBS), then layered over HISTOPAQUE ® 1077 (a density gradient medium commerically available from Sigma-Aldrich Biotechnology LP, St. Louis, MO), and the layered material is centrifuged at 400×g for 45 min. The PBMC are collected and washed with PBS. The washed PBMC are mixed with 20% fetal bovine serum and 10% dimethyl sulfoxide and frozen in liquid nitrogen. Prior to use, the challenge stock is diluted with buffered saline solution to a final dilution of 1:3 or 1:4 challenge stock:buffered saline solution.

B. Challenge Method

In this evaluation, 20 dogs ranging in age from 8 to 12 months are randomized into 2 groups. The dogs are challenged via the subcutaneous route with 1 mL of the diluted challenge stock. One group is challenged with a 1:3 dilution of challenge stock and the remaining group is challenged with a 1:4 dilution of challenge stock. After challenge, the dogs are observed and blood samples are taken 3×per week in order to monitor the clinical signs of disease, including thrombocytopenia, for a total of 56 days.

C. Observations

The clinical signs observed included mucopurulent nasal and ocular discharges, depression, dehydration, lymphadenopathy and corneal edema. The mucopurulent ocular discharges and dehydration are the most frequent signs observed. The mucopurulent ocular discharges and dehydration are specific with the disease progress and indirectly reflect the severity of the disease. One incidence per observation time point for each clinical sign is recorded and the total incidence between the groups is compared. Of the observed time points, 53% (1:3 dilution) and 35% (1:4 dilution) had mucopurulent ocular discharge and 44% (1:3 dilution) and 30% (1:4) had dehydration.

A significantly high mortality rate was also observed in this evaluation. The induction of mortality is the most striking indication of the potent pathogenesis of the *E. canis* bacterin used in the challenge stock. For the 1:3 dilution treatment, 100% of the dogs met the case definition of ehrlichiosis and for the 1:4 dilution treatment, 80% met the case definition of ehrlichiosis. The data are shown in Table I.

Rectal temperatures were recorded as an indicator of *ehrlichia* infection. Most of the infected dogs had some incidences of elevated rectal temperature. The data are shown in Table II.

Thrombocytopenia (blood platelet counts below 200,000/μL) was observed starting at about 12 days post challenge (DPC) and throughout the remainder of the observed period. The data are shown in Table III.

D. Conclusions

The challenge model described hereinabove produces severe clinical signs of canine ehrlichiosis in dogs and provides a case definition of ehrlichiosis disease for use in further study and evaluation of treatments therefor. The clinical case definition of canine ehrlichiosis will be defined by mortality, at least three consecutive observation days of mucopurulent ocular discharge and/or at least three consecutive observation days of dehydration.

TABLE I

| Dilution | Clinical Signs | Number of animals with signs for 3 consecutive days | % of animals with signs for 3 consecutive days | Average duration of clinical signs | Total incidence of itemized clinical signs |
|---|---|---|---|---|---|
| 1:3 | Mucopurulent Nasal Discharge | 1/10 | 10% | 0.5 days | 5 |
| 1:3 | Mucopurulent Ocular Discharge* | 7/10 | 70% | 4.8 days | 48 |
| 1:3 | Depression | 2/10 | 20% | 1.1 days | 11 |
| 1:3 | Dehydration* | 6/10 | 60% | 4.0 days | 40 |
| 1:3 | Lymphadenopathy | 0 | 0 | 0 | 0 |
| 1:3 | Corneal Edema | 1/10 | 10% | 1.2 days | 12 |
| 1:3 | Death* | 9/10 | 90% | | |
| 1:4 | Mucopurulent Nasal Discharge | 0 | 0 | 0.1 days | 1 |
| 1:4 | Mucopurulent Ocular Discharge* | 7/10 | 70% | 3.8 days | 40 |
| 1:4 | Depression | 0 | 0 | 0.7 days | 7 |
| 1:4 | Dehydration* | 5/10 | 50% | 3.4 days | 34 |
| 1:4 | Lymphadenopathy | 0 | 0 | 0 | 0 |
| 1:4 | Corneal Edema | 1/10 | 10% | 0.5 day | 5 |
| 1:4 | Death* | 4/10 | 40% | | NA |

*Signs are included in the case definition of ehrlichiosis.

TABLE II

Rectal Temperature ° F. - Post Challenge

| Dilution | 12 Days | 14 Days | 28 Days | 42 Days | 56 Days |
|---|---|---|---|---|---|
| 1:3 | 104.7 | 105.7 | NA | NA | NA |
| 1:3 | 103.1 | 103.2 | 102.6 | 99.2 | NA |
| 1:3 | 102.2 | 103.0 | 103.5 | NA | NA |
| 1:3 | 102.9 | 102.9 | 102.2 | 90.1 | NA |
| 1:3 | 102.2 | 102.7 | 103.6 | 102.1 | NA |
| 1:3 | 102.5 | 103.0 | 104.5 | 101.5 | NA |
| 1:3 | 104.4 | 104.1 | 104.8 | 102.8 | 101.9 |
| 1:3 | 103.2 | 103.0 | 104.1 | 101.0 | NA |
| 1:3 | 102.6 | 102.6 | 105.0 | 101.1 | NA |
| 1:3 | 103.5 | 102.7 | 102.6 | 103.3 | 101.9 |
| 1:4 | 102.3 | 101.8 | 105.1 | 102.1 | NA |
| 1:4 | 102.9 | 102.9 | 104.0 | 91.2 | NA |
| 1:4 | 102.1 | 102.4 | 104.9 | 101.5 | 101.5 |
| 1:4 | 102.9 | 102.1 | 103.7 | 102.0 | 101.7 |
| 1:4 | 102.6 | 102.5 | 105.2 | 102.6 | 101.8 |
| 1:4 | 102.0 | 102.2 | 103.9 | 103.0 | 101.0 |
| 1:4 | 103.5 | 104.2 | 103.0 | 101.6 | NA |
| 1:4 | 102.9 | 103.1 | 101.2 | 102.5 | 101.1 |
| 1:4 | 101.8 | 102.0 | 105.4 | 103.0 | 101.2 |
| 1:4 | 103.3 | 103.8 | 103.7 | NA | NA |

TABLE III

Blood Platelet Counts, $10^3/\mu L$ - Post Challenge

| Dilution | 0 Days | 12 Days | 14 Days | 19 Days | 21 Days | 26 Days | 28 Days | 33 Days | 39 Days | 56 Days |
|---|---|---|---|---|---|---|---|---|---|---|
| 1:3 | 407 | 155/185 | 101/91.4 | 1.42/2.95 | .599/1.24 | NA | NA | NA | NA | NA |
| 1:3 | 301 | 269 | 164/126 | 3.3/1.16 | 4.76/4.9 | 48.7/50.5 | 55.5 | 78.3 | 4 | NA |
| 1:3 | 497 | 321 | 135/164 | 57.7/41.6 | 53.8/56.2 | 107/105 | 120.0 | 163 | 54.3 | NA |
| 1:3 | 534 | 458 | 293 | 2.03/1.29 | .426/1.87 | 14.6/31.6 | 8.06 | 4 | 5.78 | NA |
| 1:3 | 308 | 260 | 205 | 33.2/20.1 | 9.59/7.31 | 6.13/1.89 | 5.9 | 52 | 38.6 | NA |
| 1:3 | 300 | 374 | 329 | 79.2/83 | 3.47/2.84 | 0/.698 | 2.99 | 0.788 | .55 | NA |
| 1:3 | 398 | 360 | 221 | 51.4/41.1 | 50.3/49.6 | 4.42/6.21 | 54.6 | 87.1 | 62 | 33.8 |
| 1:3 | 464 | 413 | 306 | 39.2/38 | 6.38/6.56 | 55.3/39.3 | 58.3 | 97 | 3.17 | NA |
| 1:3 | 281 | 225 | 139/143 | 1.9/1.41 | 0/0 | 5.5/3.55 | 7.3 | 2.61 | 4.2 | NA |
| 1:3 | 263 | 400 | 161/162 | .446/.388 | .612/.741 | 7.41/9.23 | 7.31 | 8.89 | 4.82 | 86.4 |
| 1:4 | 343 | 342 | 378 | 287 | 139/130 | 2.71/4.11 | 1.58 | 44.9 | 59.9 | NA |
| 1:4 | 411 | 343 | 246 | 1.61/2.19 | 1.74/.795 | 8.58/19.8 | 6.37 | 2 | .887 | NA |
| 1:4 | 329 | 434 | 452 | 172/193 | 109/122 | 5.45/3.08 | 3.5 | 2.47 | 1.99 | 0.0 |
| 1:4 | 283 | 289 | 156/152 | 98.1/106 | 50.4/61.6 | 6.25/3.84 | 13.2 | 56.7 | 57.1 | 50.8 |
| 1:4 | 286 | 269 | 207 | 63.9/63 | 13.6/11.3 | 104/97.2 | 18.1 | 55.9 | 56.4 | 68.7 |
| 1:4 | 445 | 609 | 490 | 165/190 | 89.3/84.6 | 43.1/42.3 | 3.32 | 1.84 | 1.89 | 51.3 |
| 1:4 | 306 | 284 | 146/141 | 73.8/54.2 | 30.2/21.2 | 8.62/5.07 | 12.2 | 9.8 | 3.73 | NA |
| 1:4 | 315 | 231 | 204 | 38.9/9.96 | 4.73/2.34 | 3.17/4.86 | 10.7 | 5.37 | 1.08 | 81.1 |
| 1:4 | 296 | 249 | 380 | 296 | 228 | 55.1/51.1 | 42.6 | 82.9 | 59 | 93.1 |
| 1:4 | 317 | 281 | 153/182 | 2.07/.689 | 4.5/5.78 | 8.58/8.37 | 8.18 | 46.1 | NA | NA |

EXAMPLE 2

Evaluation of the Efficacy Induced by BCG Adjuvanted *E. canis* Bacterin

BCG, an autoclaved preparation of attenuated *mycobacterium bovis* is recognized as a potent inducer of cell-mediated immunity (CMI). To determine the synergistic CMI effects, the *E. canis* bacterin was adjuvanted with BCG at different concentration levels. Previous studies demonstrated that the *E. canis* bacterin adjuvanted solely with conventional (antibody response inducing) canine adjuvants (such as EMA and NEOCRYL®a latex emulsion of a copolymer of styrene with a mixture of acrylic and methacrylic acid commerically available from Avecia BV, Netherlands) was only able to induce sub-potent protective immunity.

A. Materials and Methods

Three vaccination groups of 7 dogs each and a control group of 6 dogs were used. The vaccine contains 5 log $TCID_{50}$ (pre-inactivated titer) *E. canis* Ebony strain bacterin adjuvanted with the following combinations of adjuvants. Vaccine A contained *borrelia burgdoferi* bacterin (BBB) and EMA/NEOCRYL® (NEOCRYL® is a latex emulsion of a copolymer of styrene with a mixture of acrylic and methacrylic acid commerically available from Avecia BV, Netherlands). Vaccine B contained *borrelia burgdoferi* bacterin (BBB), EMA/NEOCRYL® and 100 ug/dose of BCG. Vaccine C contained *borrelia burgdoferi* bacterin (BBB), EMA/NEOCRYL® and 1.0 mg/dose of BCG. The other components of the three vaccines were identical. The control group of dogs was not vaccinated.

The 27 dogs were randomized into 4 groups. The first three groups of 7 dogs each were vaccinated twice with vaccine A, B, or C through subcutaneous route at an interval of 21 days. The fourth group of 6 dogs served as control and was not vaccinated. Sixteen days after the second vaccination, all dogs were challenged with virulent *E. canis* and observed for clinical signs, rectal temperatures and changes of blood platelet counts for a total of 56 days.

B. Results and Discussion

The results are summarized in Table IV. Fifty-six days after virulent *E. canis* challenge, four out of 7 (57%) dogs were thrombocytopenic and had high rectal temperatures in the vaccine A inoculated group. The same results were observed in the vaccine B inoculated group. Within the dogs in the vaccine C group, only two of 7 (28.5%) vaccinated dogs had thrombocytopenia and high rectal temperature during the study. Five out of 6 (83%) control dogs had thrombocytopenia and high rectal temperatures. The clinical signs of each group were mixed and had no difference between the groups. The changes in body temperatures and thrombocyte counts were typical signs of *E. canis* infection and ehrlichiosis.

TABLE IV

| Group | Vaccine components | Number of dogs with thrombocytopenia | Number of dogs with Temperature |
|---|---|---|---|
| Vaccine A | *E. canis* bacterin + BBB[1] + EMA[2]/NEOCRYL ® A640[3] | 4 out of 7 dogs (57%) | 4 out of 7 dogs (57%) |
| Vaccine B | *E. canis* bacterin + BBB + EMA/NEOCRYL ® A640 + 100 ug/dose BCG[4] | 4 out of 7 dogs (57%) | 4 out of 7 dogs (57%) |
| Vaccine C | *E. canis* bacterin + BBB + EMA/NEOCRYL ® A640 + 1.0 mg/dose BCG | 2 out of 7 dogs (28.5%) | 2 out of 7 dogs (28.5%) |
| Control | None | 5 out of 6 dogs (83%) | 5 out of 6 dogs (83%) |

[1]BBB = *borrelia burgdoferi* bacterin sourced from Fort Dodge Animal Health production serials.
[2]An ethylene-maleic anhydride copolymer manufactured by Monsanto Co., St. Louis, MO.
[3]A latex emulsion of a copolymer of styrene with a mixture of acrylic and methacrylic acid manufactured by AVECIA Neo Resius, Frankfort, IN
[4]BCG = Bacille Calmette-Guérin, which is attenuated *mycobacterium bovis*, sourced from Calbiochem, La Jolla, CA.

The results from this study clearly showed that the vaccine adjuvanted solely with conventional (antibody response inducing) adjuvant (EMA+NEOCRYL®) was not protective. The same was true when the vaccine was adjuvanted with lower dose of BCG, such as 100 ug/dose. However, the vaccine became protective when it was adjuvanted with 1 mg/dose of BCG. Thus, the protective immunity induced by a CMI inducer, BCG, at a sufficient concentration to enhance the immune response, results in *E. canis* bacterin vaccine efficacy.

C. Conclusion

CMI is necessary to protect dogs from *E. canis* infection. The *E. canis* bacterin adjuvanted solely with a conventional canine adjuvant is not effective in inducing protective immunity in vivo.

EXAMPLE 3

Preparation of an Inactivated *E. canis* Vaccine Composition

Two strains of *E. canis* bacterin, Ebony and Broadfoot, are each cultivated in DH82 cells supported by a medium containing RPMI1640 supplemented with 5% to 7% fetal bovine serum, 2% glucose and 2 mmole glutamine for 5 to 14 days. The resultant cultures are harvested at a titer of $\geqq 1\times10^4$ $TCID_{50}$. The harvests are titrated, lysed, and then inactivated by adding an 0.1% formalin solution, incubating at 36°±2C for a period of 24-48 hours, adding another portion of 0.1% formalin and incubating a second time at 36°±C. for 24-48 hours. The two inactivated strains of *E. canis* are blended together at an equal dosage of $1\times10^{45}$ $TCID_{50}$ with the adjuvant system described below to give vaccine composition A.

| Vaccine Composition A | |
| --- | --- |
| Ingredient Description | Amount per mL |
| Inactivated E. canis, Ebony | $1 \times 10^{4.5}$ TCID$_{50}$ |
| Inactivated E. canis, Broadfoot | $1 \times 10^{4.5}$ TCID$_{50}$ |
| EMA[1]-31 | 1% vol/vol |
| NEOCRYL ®[2] A-640 | 3% vol/vol |
| EMULSIGEN ®[3] SA | 5% vol/vol |
| MEM[4] | QS to 100% |

[1] An ethylene-maleic anhydride copolymer manufactured by Monsanto Co., St. Louis, MO.
[2] A latex emulsion of a copolymer of styrene with a mixture of acrylic and methacrylic acid manufactured by AVECIA Neo Resius, Frankfort, IN
[3] A paraffin oil-in-water emulsion manufactured by MVP Laboratories, Inc., Ralston, NE
[4] Minimum Essential Medium (MEM) manufactured by LTI, Grand Island, NY

EXAMPLE 4

Evaluation of Twelve Month Duration of Immunity Induced by E. canis Vaccine Composition A In this evaluation, 15- to 16-week old beagles are divided into 2 groups, a control (unvaccinated) group of 15 dogs and a vaccinated group of 27 dogs. The vaccinated group receives two 1 mL doses of the vaccine composition A, described in Example 3, at an interval of 21 days. Twelve months after vaccination, all test animals are challenged with a 1:3 dilution of an established frozen challenge pool of E. canis infected peripheral blood mononuclear cells (pmbc), as described in Example 1, by the subcutaneous route. The test animals are observed 3×per week starting at 12 days post challenge (DPC). In compliance with animal welfare and Institutional Animal Care and Use Committee (IACUC) guidelines, any test animal that is moribund or of poor body condition is closely examined by state licensed veterinarians.

Serum samples are evaluated for E. canis antibodies using a K-ELISA to quantitate the immune response following vaccination. The serum samples are added in duplicate to wells coated with E. canis whole cell extract protein. Peroxidase-conjugated goat anti-dog immunoglobulin (IgG) is then added to each well and the plates are incubated at 36°±2° C. for 30 minutes. After removal of unbound conjugate, the plates are developed using an ATBS substitute system. The plates are read at 405-490 µm for 20 minutes at 35-second intervals using a kinetic mode. The serological results are shown in Table V wherein DPVI designates days post-first dose of vaccine; DPV2 designates days post-second dose of vaccine; MPV2 designates months post-second dose of vaccine; and DPC designates days post challenge.

Observations

As can be seen from the serological data in Table V, the vaccinated group showed a significant increase in antibodies over the control (unvaccinated) group. A significant difference in antibodies between the vaccinated and control groups is also observed post challenge. In addition to serological data, hematocrit values, platelet counts, rectal temperatures and weekly body weights are recorded. The hematocrit percentage was significantly less lowered in the vaccinated group as compared to the control group. The platelet counts were significantly less lowered in the vaccinated group as compared to the control group by 44 days post challenge. The weight loss was significantly less in the vaccinates when compared to the controls. In the control group, 87 percent met the case definition for canine ehrlichiosis, including mortality. In the vaccinated group, 44 percent met the case definition for canine ehrlichiosis during the 56-day clinical observation period.

Conclusions

The E. canis vaccine composition of Example 3 significantly reduces clinical canine ehrlichiosis in dogs. Administration of two 1 mL doses of said vaccine induces immunity over a period of at least 12 months. A significant increase in antibodies against E. canis in dogs is obtained by the administration of the vaccine composition of Example 3.

TABLE V

Antibody Response to Inactivated E. canis Vaccine

| Treatment Group | 0 DPV1 | 0 DPV2 | 14 DPV2 | 3 MPV2 | 5 MPV2 | 9 MPV2 | 0 DPC | 14 DPC |
| --- | --- | --- | --- | --- | --- | --- | --- | --- |
| Control | 0.000 | 0.000 | 0.000 | 0.072 | 0.054 | 0.052 | 0.030 | 1.024 |
| Control | 0.036 | 0.006 | 0.003 | 0.006 | 0.003 | 0.000 | 0.007 | 0.773 |
| Control | 0.036 | 0.007 | 0.005 | 0.000 | 0.006 | 0.000 | 0.004 | 0.899 |
| Control | 0.000 | 0.000 | 0.018 | 0.000 | 0.003 | 0.000 | 0.000 | 0.800 |
| Control | 0.112 | 0.027 | 0.000 | 0.002 | 0.005 | 0.000 | 0.000 | 0.916 |
| Control | 0.089 | 0.011 | 0.023 | 0.000 | 0.000 | 0.005 | 0.003 | 0.426 |
| Control | 0.006 | 0.001 | 0.002 | 0.002 | 0.000 | 0.001 | 0.002 | 0.186 |
| Control | 0.188 | 0.065 | 0.044 | 0.027 | 0.020 | 0.019 | 0.015 | 0.426 |
| Control | 0.054 | 0.028 | 0.021 | 0.000 | 0.003 | 0.002 | 0.000 | 0.915 |
| Control | 0.008 | 0.000 | 0.000 | 0.006 | 0.000 | 0.002 | 0.000 | 0.442 |
| Control | 0.072 | 0.011 | 0.000 | 0.004 | 0.004 | 0.005 | 0.000 | 0.364 |
| Control | 0.014 | 0.004 | 0.000 | 0.002 | 0.000 | 0.000 | 0.000 | 0.536 |
| Control | 0.223 | 0.098 | 0.057 | 0.008 | 0.009 | 0.006 | 0.022 | 0.675 |
| Control | 0.064 | 0.057 | 0.033 | 0.002 | 0.001 | 0.001 | 0.003 | 0.168 |
| Control | 0.034 | 0.014 | 0.004 | 0.002 | 0.001 | 0.001 | 0.000 | 0.068 |
| Average | 0.062 | 0.022 | 0.014 | 0.009 | 0.007 | 0.006 | 0.006 | 0.574 |
| Vaccinated | 0.022 | 0.825 | 0.976 | 0.503 | 0.422 | 0.349 | 0.294 | 1.016 |
| Vaccinated | 0.028 | 0.533 | 0.951 | 0.245 | 0.113 | 0.118 | 0.121 | 0.859 |
| Vaccinated | 0.074 | 0.810 | 0.966 | 0.361 | 0.216 | 0.236 | 0.159 | 0.964 |
| Vaccinated | 0.035 | 0.307 | 0.924 | 0.246 | 0.146 | 0.137 | 0.091 | 0.947 |
| Vaccinated | 0.052 | 0.377 | 0.636 | 0.070 | 0.034 | 0.034 | 0.036 | 0.663 |
| Vaccinated | 0.000 | 0.303 | 0.889 | 0.143 | 0.107 | 0.067 | 0.077 | 0.768 |
| Vaccinated | 0.061 | 0.335 | 0.740 | 0.097 | 0.122 | 0.084 | 0.061 | 0.831 |
| Vaccinated | 0.005 | 0.403 | 0.949 | 0.224 | 0.191 | 0.227 | 0.172 | 0.772 |

TABLE V-continued

Antibody Response to Inactivated *E. canis* Vaccine

| Treatment Group | 0 DPV1 | 0 DPV2 | 14 DPV2 | 3 MPV2 | 5 MPV2 | 9 MPV2 | 0 DPC | 14 DPC |
|---|---|---|---|---|---|---|---|---|
| Vaccinated | 0.038 | 0.477 | 0.885 | 0.122 | 0.097 | 0.158 | 0.124 | 0.599 |
| Vaccinated | 0.020 | 0.407 | 0.816 | 0.075 | 0.059 | 0.079 | 0.045 | 0.633 |
| Vaccinated | 0.042 | 0.463 | 0.853 | 0.167 | 0.101 | 0.050 | 0.061 | 0.886 |
| Vaccinated | 0.032 | 0.648 | 0.945 | 0.278 | 0.187 | 0.185 | 0.177 | 1.002 |
| Vaccinated | 0.050 | 0.150 | 0.745 | 0.196 | 0.127 | 0.103 | 0.071 | 0.593 |
| Vaccinated | 0.135 | 0.652 | 0.856 | 0.139 | 0.080 | 0.054 | 0.062 | 0.866 |
| Vaccinated | 0.061 | 0.268 | 0.900 | 0.231 | 0.133 | 0.089 | 0.075 | 0.711 |
| Vaccinated | 0.119 | 0.606 | 0.893 | 0.243 | 0.184 | 0.125 | 0.101 | 0.761 |
| Vaccinated | 0.039 | 0.335 | 0.888 | 0.113 | 0.062 | 0.056 | 0.047 | 0.734 |
| Vaccinated | 0.015 | 0.231 | 0.911 | 0.120 | 0.068 | 0.051 | 0.061 | 0.743 |
| Vaccinated | 0.030 | 0.390 | 0.957 | 0.108 | 0.085 | 0.094 | 0.048 | 0.773 |
| Vaccinated | 0.008 | 0.295 | 0.879 | 0.290 | 0.209 | 0.121 | 0.196 | 0.828 |
| Vaccinated | 0.055 | 0.262 | 0.737 | 0.105 | 0.065 | 0.076 | 0.060 | 0.531 |
| Vaccinated | 0.041 | 0.297 | 0.989 | 0.306 | 0.089 | 0.052 | 0.145 | 0.873 |
| Vaccinated | 0.013 | 0.226 | 0.826 | 0.167 | 0.090 | 0.066 | 0.051 | 0.706 |
| Vaccinated | 0.058 | 0.180 | 0.518 | 0.193 | 0.146 | 0.093 | 0.113 | 0.881 |
| Vaccinated | 0.065 | 0.103 | 0.386 | 0.050 | 0.036 | 0.013 | 0.000 | 0.518 |
| Vaccinated | 0.030 | 0.159 | 0.543 | 0.154 | 0.168 | 0.102 | 0.056 | 0.416 |
| Vaccinated | 0.105 | 0.222 | 0.364 | 0.122 | 0.084 | 0.039 | 0.041 | 0.268 |
| Average | 0.046 | 0.380 | 0.812 | 0.188 | 0.127 | 0.106 | 0.094 | 0.746 |

EXAMPLE 5

Evaluation of Cell-Mediated Immunity in Response to Inactivated *E. canis* Vaccine Canine IL-12 and IFN-γ Elispot assays are used to evaluate the levels of IL-12 and IFN-γ in dogs vaccinated with *Ehrlichia canis* (*E. canis*) bacterin. In comparison to control dogs, the higher number of IL-12 and IFN-γ spots produced by peripheral blood mononuclear cells isolated from vaccinated dogs indicates that a CMI response may play a role in the protection against *E. canis* infection.

A. Materials and Methods

Two groups of dogs are used in this study: Vaccinates that received the *E. canis* bacterin and controls, which did not receive the bacterin. Whole blood is drawn from vaccinated and control dogs after the first vaccination with *E. canis* bacterin. Whole blood samples from the control and vaccinated dogs are collected via sterile venipuncture into 10 mL EDTA tubes. Peripheral blood mononuclear cells (PBMC) are isolated by centrifugation on a Percoll gradient. After isolation, PBMC are counted and the cell concentration is determined for each sample. Isolated PBMC are then used immediately for an Elispot assay.

The complete culture medium used for culturing canine PBMC consists of equal volumes of Aim V (Invitrogen, Carlsbad, Calif.; Cat. # 12055-083) and Ex-Cell (JRH Biosciences, Lenexa, Kans.; Cat. # 141610-500M), 10% heat inactivated equine serum (Hyclone, Logan, Utah; Cat. # SH30074.03) and 10 μg/mL gentamycin.

Elispot Assay

Preparation of Elispot Plates

IL-12 Plates

Immobilon P plates (Millipore, Burlington, Mass.) are pre-wetted with 70% methanol, washed with Dulbecco-Vogt phosphate buffered saline (DPBS), coated with 100 μL/well of mouse anti-human IL-12 antibody (10 μg/mL; Mabtech, Sweden), diluted in carbonate buffer, pH 9.6, and incubated at 37° C., 5±2% $CO_2$ for 2 hours. Plates are then washed with DPBS+0.1% TWEEN® 20 (an emulsifying agent polysorbate available from Sigma Chemical Co., St. Louis, MO) and blocked with complete Aim V/ExCell medium at 36° C., 5±2% $CO_2$ for a minimum of 2 hours.

IFN-γ Plates

Elispot plates for canine IFN-γ detection are prepared in a similar manner to canine IL-12 plates, using an antibody specific for canine IFN-γ. The plates used in this study are purchased from R&D Systems (Minneapolis, Minn.; Cat. # EL781) and prepared according to the manufacturer's instruction. These plates are pre-coated with anti-canine IFN-γ polyclonal antibody.

Preparation of Antigens

Six different cell preparations are initially used as antigens to stimulate IL-12 and IFN-γ production. They include:
 1. Live *E. canis* infected DH82 cells
 2. *E. canis* infected DH82 cell lysate (cells were lyzed by homogenization)
 3. *E. canis* infected DH82 cell lysate inactivated by formalin treatment
 4. Live un-infected DH82 cells alone
 5. Un-infected DH82 cell lysate
 6. Un-infected DH82 cell lysate inactivated by formalin treatment.

The first three preparations are used to stimulate IL-12 and IFN-γ production. The second three preparations are used as negative controls in the test. On the day of the assay, live *E. canis* infected and un-infected DH82 cells are harvested, counted, and the cell concentration determined. The desired number of live cells and the equivalent cell numbers of cell lysate (treated with or without formalin) are resuspended in the complete Aim V/Excell culture medium and applied to the assay. The mitogens Concanavalin A (Con A) Sigma Cat# C0412 and Lectin from *Phaseolus vulgaris* (PHA) Sigma Cat.# L-4144 are prepared in the complete culture medium and used as positive controls for the assay.

Incubation of *E. canis* and PBMC

The antibody coated plates, following the 2 hour medium blocking, are washed with Dulbecco's phosphate-buffered saline (DPBS)+0.1% TWEEN® 20 (an emulsifying agent polysorbate available from Sigma Chemical Co., St. Louis, MO). Live E. canis infected and un-infected DH82 cells, cell lysates, medium and positive control at appropriate dilution are added to the antibody coated wells in volumes of 150 μL per well. Diluted PBMC that have been diluted to a desired cell concentration in the complete culture medium and 50 μL/well of cell culture are added into the appropriate wells. The plates are then incubated at 36° C.±2° C., 5±2% $CO_2$ from 20 to 50 hours depending on the assay being performed.

Plate Development

IL-12 Plates

After incubation, the cells are removed by washing with DPBS+0.1% TWEEN® 20 (an emulsifying agent polysorbate available from Sigma Chemical Co., St. Louis, MO). Biotinylated detection antibody (Mabtech, Sweden; Cat. #3450-6) is diluted in DPBS+0.5% bovine serum albumin (BSA) at 1.0 μg/mL and filtered through a 0.2 μm syringe filter prior to use. 100 μL of detection antibody is added to appropriate wells. The plates are incubated at 36° C.±2° C., 5±2% $CO_2$ for three hours. The detection antibody is removed and the plates are washed with DPBS+0.1% TWEEN®. The plates are incubated with 100 μL/well StreptAvidin-HRP (KPL, Gaithersburg, Md.; Cat. # 14-30-00) diluted at 1:1000 in DPBS+0.1% Tween 20 at 36° C., 5±2% $CO_2$ for 1 hour.

During incubation, the substrate solution is prepared. One 20 mg tablet of AEC (3-Amino-9-Ethy-Carbazole, Sigma, St. Louis, Mo.; Cat. # D4254) is dissolved in 2 mL N,N-Dimethylformamide (DNF) in a glass Erylenmeyer flask. Once dissolved, 58 mL of 0.1M sodium acetate (pH 5.0) and 30 μL hydrogen peroxide ($H_2O_2$) are added to the substrate solution, which is then filtered through a 0.45 μm filter prior to use.

The plates are washed with DPBS+0.1% Tween® 20(an emulsifying agent polysorbate available from Sigma Chemical Co., St. Louis, MO), followed by a wash with DPBS alone to remove residual detergent. One hundred μL of substrate solution are added to each well and incubated at room temperature for a maximum of 20 minutes. The reaction is stopped by removing the substrate solution and rinsing with distilled water. The plates are dried at room temperature and the spot-producing units (SPC) are evaluated for quantity, area, and intensity using a Zeiss Elispot Reader (Carl Zeiss Vision, Oberkochen, Germany) with KS ELISPOT 4.4 software.

IFN-γ Plate

After incubation, the cells are removed by washing with wash buffer (R&D Systems, Minneapolis, Minn.). Biotinylated detection antibody is diluted in dilution buffer 1 (R&D System, Minneapolis, Minn.) according to the manufacturer's instructions and filtered through a 0.2 μm syringe filter prior to use. One hundred μL of detection antibody are added to appropriate wells. The plates are then incubated at 36° C.±2° C., 5±2% $CO_2$ for three hours. The detection antibody is removed and the plates are washed with wash buffer. The plates are incubated with 100 μL/well StreptAvidin-AP diluted according to the manufacturer's instruction (R&D System, Minneapolis, Minn.) at 36° C.±2° C., 5±2% $CO_2$ for 1 hour.

Following incubation with StreptAvidin-AP, the plates are washed with wash buffer and incubated with 100 μL per well BCIP/NBT (R&D System, Minneapolis, Minn.) at room temperature for 20 minutes. Removing the substrate solution and rinsing the plate with distilled water stops the reaction. The plates are dried at room temperature and the spot-producing units (SPC) are evaluated for quantity, area, and intensity using a Zeiss Elispot Reader (Carl Zeiss Vision, Oberkochen, Germany) with KS ELISPOT 4.4 software.

Data Analysis

Results are read as spot-forming cells (SFC) and expressed differently depending on the nature of experiments. There are three possible ways to present the data: the original number of spots in each well, the average number of spots for each treatment for each sample and Stimulus Index. Stimulus Index is calculated by dividing the average number of spots in un-stimulated wells (cells+culture medium only) by the average number of spots in stimulated wells.

B. Results and Interpretation

This evaluation is performed to evaluate the number of IL-12 and IFN-γ secreting cells in PBMC isolated from E. canis vaccinated dogs.

In this experiment, one control and three vaccinated dogs are used. The results of the experiment are presented in Tables VI and VII. From Table VI, the data indicate that only live E. canis infected DH82 cells stimulated IL-12 production in PBMC in the three vaccinated dogs in comparison to no production by PBMC from the control dog. The stimulation is also dose-dependent upon E. canis infected DH82 cells, with the highest number of spots at the 1:10 dilution (equivalent to $1 \times 10^4$ cells/well) of the E. canis stock than at the 1:1000 dilution. E. canis infected DH82 cell lysate with or without formalin treatment, live un-infected DH82 cells, un-infected DH82 cell lysate, and formalin treated lysate DH82 cells did not result in any detectable IL-12 response. Two of the vaccinated dogs reacted to a higher degree than the third vaccinate. The control dog did not show a response to any stimulation except for a low response to positive mitogen (PHA).

Table VII shows the results of IFN-γ Elispots for the same four dogs. Similar to IL-12, live E. canis DH82 cells showed the highest induction of IFN-γ spots in all three vaccinated dogs. The induction is also E. canis cell number dependent, with the highest-level present at the 1:10 dilution and the lowest level at the 1:1000 dilution. The E. canis infected DH82 cell lysate resulted in lower spot number for the vaccinated dogs. The lysate treated with formalin resulted in a background at the 1:1000 dilution but no spots at the 1:10 or 1:100 dilutions. This may be due to the inhibitory effect of residual formalin on mononuclear cell activity. Un-infected DH82 cells for all three preparations yielded only background spotting in comparison to the live E. canis infected DH82 cells. The individual dog response was similar to that seen on the IL-12 Elispot. The same two vaccinated dogs showed a higher response than the third one and the control dog exhibited a low response to mitogen (Con A) stimulation alone.

The results of this experiment demonstrate that only live E. canis infected DH82 cells can induce both IL-12 and IFN-γ production by PBMC. E. canis infected DH82 cell lysate or lysate treated with formalin cannot be used because of the low stimulation effect on T cell or monocyte on cell activity.

C. Summary

The data shown in Tables VI and VII hereinbelow demonstrate that CMI may play a role in the protection of dogs vaccinated with the E. canis bacterin. Increased numbers of IL-12 and IFN-γ spots for the vaccinated dogs represent the activation of T cell and monocytes.

TABLE VI

IL-12 Elispot Response in Dogs Induced by *E. canis* Bacterin

| | Antigen Dilution | | | | | | | | | | | |
|---|---|---|---|---|---|---|---|---|---|---|---|---|
| | 1:10 | 1:100 | 1:1000 | 1:10 | 1:100 | 1:1000 | 1:10 | 1:100 | 1:1000 | 1:10 | 1:100 | 1:1000 |
| *E. canis* Infected DH82 Cell Lysate | 0 | 0 | 0 | 0 | 0 | 0 | 0 | 0 | 0 | 0 | 0 | 0 |
| *E. canis* Infected DH82 Cell Lysate Inactivated | 0 | 0 | 0 | 0 | 0 | 0 | 0 | 0 | 0 | 0 | 0 | 3 |
| Un-infected DH82 Cell Lysate | 0 | 0 | 0 | 1 | 0 | 0 | 0 | 0 | 0 | 0 | 0 | 0 |
| Un-infected DH82 Cell Lysate Inactivated | 0 | 0 | 0 | 0 | 0 | 0 | 0 | 0 | 0 | 0 | 0 | 0 |
| Live *E. canis* Infected DH82 Cells | 0 | 0 | 0 | 88 | 23 | 2 | 76 | 24 | 3 | 10 | 7 | 1 |
| Live un-infected DH82 Cells | 0 | 0 | 0 | 0 | 1 | 0 | 0 | 0 | 0 | 1 | 0 | 1 |
| Unstimulated | 0 | 0 | 0 | 0 | 1 | 0 | 0 | 0 | 0 | 3 | 0 | 0 |
| Positive Control | 3 | 4 | 3 | 81 | 92 | 66 | 130 | 120 | 113 | 44 | 33 | 31 |

TABLE VII

IFN-g Elispot Response in Dogs Induced by *E. canis* Bacterin

| | Antigen Dilution | | | | | | | | | | | |
|---|---|---|---|---|---|---|---|---|---|---|---|---|
| | 1:10 | 1:100 | 1:1000 | 1:10 | 1:100 | 1:1000 | 1:10 | 1:100 | 1:1000 | 1:10 | 1:100 | 1:1000 |
| *E. canis* Infected DH82 Cell Lysate | 0 | 0 | 0 | 181 | 216 | 104 | 82 | 88 | 75 | 3 | 1 | 1 |
| *E. canis* Infected DH82 Cell Lysate Inactivated | 0 | 0 | 0 | 0 | 0 | 116 | 0 | 0 | 76 | 1 | 7 | 3 |
| Un-infected DH82 Cell Lysate | 0 | 0 | 0 | 96 | 155 | 106 | 37 | 87 | 87 | 3 | 3 | 2 |
| Un-infected DH82 Cell Lysate Inactivated | 0 | 0 | 0 | 0 | 1 | 109 | 0 | 0 | 95 | 0 | 4 | 4 |
| Live *E. canis* Infected DH82 Cells | 16 | 6 | 0 | 450 | 295 | 183 | 430 | 230 | 72 | 77 | 33 | 4 |
| Live un-infected DH82 Cells | 2 | 6 | 0 | 52 | 109 | 117 | 33 | 45 | 106 | 1 | 5 | 1 |
| Unstimulated | 0 | 0 | 0 | 77 | 52 | 64 | 90 | 76 | 68 | 3 | 1 | 1 |
| Positive Control | 33 | 44 | 61 | 270 | 305 | 262 | 210 | 187 | 186 | 281 | 303 | 255 |

What is claimed is:

1. A composition which comprises: an effective amount of an inactivated *Ehrlichia canis*, a pharmacologically acceptable carrier, and an immunogenically stimulating amount of an adjuvant system consisting of an antibody response inducing agent and a cell-mediated response inducing agent, wherein said antibody response inducing agent is selected from the group consisting of ethylene maleic anhydride, styrenated acrylic copolymer and a mixture thereof, and said cell-mediated response inducing agent is selected from the group consisting of an oil-in-water emulsion, an attenuated *Mycobacterium bovis* and a mixture thereof but not a Th1-related cytokine, wherein said inactivated *Ehrlichia canis* is selected from the group consisting of one or more *E. canis* strains designated as Ebony deposited under ATCC Accession Number PTA-5812, Broadfoot deposited under ATCC Accession Number PTA-5811 and a mixture thereof.

2. The composition according to claim 1 wherein the antibody response inducing agent is the mixture of ethylene maleic anhydride and styrenated acrylic copolymer.

3. The composition according to claim 1 wherein said inactivated *Ehrlichia canis* is present in sufficient quantity to provide at least $1\times10^4$ TCID$_{50}$ per unit dose.

4. The composition according to claim 1 wherein the antibody response inducing agent is a mixture of ethylene maleic anhydride and a styrenated acrylic copolymer that is present in the amount of about 1% vol/vol ethylene maleic anhydride and about 3% vol/vol styrenated acrylic copolymer.

5. The composition according to claim 1 wherein said oil-in-water emulsion is selected from the group consisting of a paraffin oil-in-water emulsion, an emulsion comprising squalane and a block copolymer of ethylene oxide and propylene oxide, an emulsion of Syntex Adjuvant Formulation-1, and a mixture thereof.

6. The composition according to claim 1 further comprising *Borrelia burgdorferi* bacteria.

7. The composition according to claim 1 wherein said cell-mediated response inducing agent is the oil-in-water emulsion and is present in a range of about 3% to 7% vol/vol.

8. The composition according to claim 1 wherein said cell-mediated response inducing agent is the oil-in-water emulsion and is present in an amount of about 5% vol/vol.

9. A method for the amelioration of canine ehrlichiosis in a dog, which comprises administering to said dog a composition which comprises an effective amount of an inactivated *Ehrlichia canis*, a pharmacologically acceptable carrier, and an immunogenically stimulating amount of an adjuvant system consisting of an antibody response inducing agent and a cell-mediated response inducing agent, wherein said antibody response inducing agent is selected from the group consisting of ethylene maleic anhydride, styrenated acrylic copolymer and a mixture thereof, and said cell-mediated response inducing agent is selected from the group consisting of an oil-in-water emulsion, an attenuated *Mycobacterium bovis* and a mixture thereof but not a Th1-related cytokine, wherein said inactivated *Ehrlichia canis* is selected from the group consisting of one or more *E. canis* strains designated as Ebony deposited under ATCC Accession Number PTA-5812, Broadfoot deposited under ATCC Accession Number PTA-5811 and a mixture thereof.

10. The method according to claim 9 having a composition wherein the antibody response-inducing agent is the mixture of ethylene maleic anhydride and the styrenated acrylic copolymer.

11. The method according to claim 9 having a composition wherein the cell- mediated response inducing agent is selected from the group consisting of a paraffin oil-in-water emulsion, an oil-in-water emulsion comprising squalane and a block copolymer of ethylene oxide and propylene oxide, an oil-in-water emulsion of Syntex Adjuvant Formulation-1, an attenuated *Mycobacterium bovis*, and a mixture thereof.

12. The method according to claim 9 having a composition wherein said inactivated *Ehrlichia canis* is present in sufficient amount to provide at least $1\times10^4$ TCID$_{50}$ per unit dose.

* * * * *